US011631502B2

(12) United States Patent
Hughes et al.

(10) Patent No.: US 11,631,502 B2
(45) Date of Patent: Apr. 18, 2023

(54) SIMULATION AND PATIENT-SPECIFIC SCALE TISSUE MODELLING OF THE GROWTH OF PROSTATE CANCER

(71) Applicants: The Board of Regents of The University of Texas System, Austin, TX (US); UNIVERSITY OF A CORUNA, A Coruna (ES)

(72) Inventors: Thomas J. R. Hughes, Austin, TX (US); Hector Gomez, A Coruna (ES); Guillermo Lorenzo, A Coruna (ES)

(73) Assignees: Board of Regents, The University of Texas System, Austin, TX (US); University of A Coruna, A Coruna (ES)

( * ) Notice: Subject to any disclaimer, the term of this patent is extended or adjusted under 35 U.S.C. 154(b) by 1029 days.

(21) Appl. No.: 16/327,875

(22) PCT Filed: Aug. 24, 2016

(86) PCT No.: PCT/ES2016/070609
§ 371 (c)(1),
(2) Date: Feb. 25, 2019

(87) PCT Pub. No.: WO2018/037137
PCT Pub. Date: Mar. 1, 2018

(65) Prior Publication Data
US 2019/0198177 A1    Jun. 27, 2019

(51) Int. Cl.
*G16H 50/50*    (2018.01)
*G16H 30/20*    (2018.01)
(Continued)

(52) U.S. Cl.
CPC .............. *G16H 50/50* (2018.01); *G06F 17/13* (2013.01); *G16H 30/20* (2018.01); *G16H 20/10* (2018.01); *G16H 20/40* (2018.01)

(58) Field of Classification Search
CPC ........ G16H 50/50; G16H 50/70; G16H 30/20; G16H 20/40; G16H 20/10; G06F 17/13
See application file for complete search history.

(56) References Cited

U.S. PATENT DOCUMENTS

| | | | |
|---|---|---|---|
| 2008/0193005 A1* | 8/2008 | Seghers | G06T 7/35 382/131 |
| 2010/0305928 A1* | 12/2010 | Cohen | G16H 50/50 703/11 |
| 2015/0216496 A1* | 8/2015 | Lee | A61B 6/466 600/425 |

OTHER PUBLICATIONS

Liu Y, Sadowski SM, Weisbrod AB, Kebebew E, Summers RM, Yao J. Patient specific tumor growth prediction using multimodal images. Medical image analysis. Apr. 1, 2014;18(3):555-66. (Year: 2014).*

(Continued)

*Primary Examiner* — Chuen-Meei Gan
(74) *Attorney, Agent, or Firm* — Kowert, Hood, Munyon, Rankin & Goetzel, P.C.; Gareth M. Sampson (57) ABSTRACT

In an embodiment, a simulation of the evolution of a tumor in a prostate gland of a subject is based at least on a coupled system of reaction-diffusion equations and a patient-specific geometric model of the prostate gland of the subject. The use of reaction-diffusion equations and a patient-specific geometric model provides a tumor model that predicts the expected progression of prostate cancer in the subject. The tumor model may be used to devise a customized treatment for the subject.

19 Claims, 6 Drawing Sheets

(51) Int. Cl.
G06F 17/13 (2006.01)
G16H 20/10 (2018.01)
G16H 20/40 (2018.01)

(56) References Cited

OTHER PUBLICATIONS

Crouch JR, Pizer SM, Chaney EL, Hu YC, Mageras GS, Zaider M. Automated finite-element analysis for deformable registration of prostate images. IEEE transactions on medical imaging. Oct. 1, 2007;26(10):1379-90. (Year: 2007).*
Peng Y, Shen D, Liao S, Turkbey B, Rais-Bahrami S, Wood B, Karademir I, Antic T, Yousef A, Jiang Y, Pinto PA. MRI-based prostate volume-adjusted prostate-specific antigen in the diagnosis of prostate cancer. Journal of Magnetic Resonance Imaging. Dec. 2015;42(6):1733-9. (Year: 2015).*
Hughes, et al., Isogeometric analysis: CAD, finite elements, NURBS, exact geometry and mesh refinement. Computer Methods in Applied Mechanics and Engineering, (2005), 194(39):4135-4195.
Bazilevs, et al., Isogeometric analysis using T-splines. Computer Methods in Applied Mechanics and Engineering, (2010), 199(5):229-263.
Scott, et al., Isogeometric spline forests. Computer Methods in Applied Mechanics and Engineering, (2014), 269:222-264.
Thomas, et al., Bezier projection: A unified approach for local projection and quadrature-free refinement and coarsening of NURBS and T-splines with particular application to isogeometric design and analysis. Computer Methods in Applied Mechanics and Engineering, (2015), 284:55-105.
Zhang, et al., Patient-specific vascular NURBS modeling for isogeometric analysis of blood flow. Computer Methods n Applied Mechanics and Engineering, (2007), 196(29):2943-2959.
Zhang, et al., Quality meshing of implicit solvation models of biomolecular structures. Computer Aided Geometric Design, (2006), 23(6):510-530.
Pennacchietti, et al. Hypoxia promotes invasive growth by transcriptional activation of the met protooncogene. Cancer Cell, (2003), 3(4):347-361.
Harma, et al., A comprehensive panel of three-dimensional models for studies of prostate cancer growth, invasion and drug responses. (2010), PLoS One 5(5):e10431.
Noguchi, et al., Assessment of morphometric measurements of prostate carcinoma volume. (2000), Cancer 89 (5):1056-1064.
Sandler, et al., Multiparametric-MRI and targeted biopsies in the management of prostate cancer patients on active surveillance. (2015), Front Oncol 5:4.
Perez-Garcia, et al., Delay effects in the response of low-grade gliomas to radiotherapy: a mathematical model and its therapeutically implications. (2015), Math Med Biol 32(3):307-329.
Corwin, et al., Toward patient-specific, biologically optimized radiation therapy plans for the treatment of glioblastoma. (2013), PLoS One 8(11):e79115.
International Search Report and Written Opinion issued in PCT/ES2016/070609 dated May 23, 2017.
Altrock, et al., "The mathematics of cancer: integrating quantitative models", Nature Reviews. Cancer, vol. 15, No. 12; Nov. 24, 2015, pp. 730-745.
Xu, et al., "A Mathematical Model Coupling Tumor Growth and Angiogenesis", PLOS ONE, vol. 11, No. 2, Feb. 18, 2016, p. e0149422.
Anderson, et al., "Tumor Morphology and Phenotypic Evolution Driven by Selective Pressure from the Microenvironment", Cell, vol. 127, No. 5, Dec. 1, 2006, p. 905-915.
Lorenzo, et al., "Tissue-scale, personalized modeling and simulation of prostate cancer growth", Proceedings National Academy of Sciences PNAS, vol. 113, No. 48, Nov. 16, 2016, p. E7663-E7671.
Taylor, et al., Predictive medicine: computational techniques in therapeutic decision-making. (1999), Comput Aided Surg 4(5):231-247.

Taylor, et al., Patient-specific modeling of cardiovascular mechanics. (2009), Annu Rev Biomed Eng 11:109-134.
Sanga, et al., Predictive oncology: A review of multidisciplinary, multiscale in silico modeling linking phenotype, morphology and growth (2007), Neuroimage 37(Suppl.1):S120-S134.
Gatenby, et al., Mathematical oncology: cancer summed up. (2003), Nature 421(6921):321.
Chauviere, et al., Mathematical oncology: how are the mathematical and physical sciences contributing to the war on breast cancer? (2010), Curr Breast Cancer Rep 2(3):121-129.
Anderson, et al., Integrative mathematical oncology. (2008), Nat Rev Cancer 8(3):227-234.
Deisboeck, et al., In silico cancer modeling: is it ready for prime time?. (2009), Nat Rev Clin Oncol 6(1):34-42.
Byrne, Dissecting cancer through mathematics: from the cell to the animal model. (2010), Nat Rev Cancer 10 (3):221-230.
Khain, Dynamics and pattern formation in invasive tumor growth. (2006), Phys Rev Lett 96(18):188103.
Frieboes, et al., Computer simulation of glioma growth and morphology. (2007), Neuroimage 37(Suppl.1):S59-S70.
Harpold, et al., The evolution of mathematical modeling of glioma proliferation and invasion. (2007), J Neuropathol Exp Neurol 66(1):1-9.
Jain, et al., Mathematical modeling of prostate cancer progression in response to androgen ablation therapy. (2011), Proc Natl Acad Sci USA 108(49):19701-19706.
Morken, et al., Mechanisms of resistance to intermittent androgen deprivation in patients with prostate cancer identified by a novel computational method. (2014), Cancer Res 74(14):3673-3683.
Kronik, et al., Predicting outcomes of prostate cancer immunotherapy by personalized mathematical models. (2010), PLoS One 5(12):e15482.
Walsh, Surgery and the reduction of mortality from prostate cancer. (2002), N Engl. J Med 347(11):839-840.
Hegde, et al., Multiparametric MRI of prostate cancer: An update on state-of-the-art techniques and their performance in detecting and localizing prostate cancer. (2013), J Magn Reson Imaging. 37(5):1035-1054.
Turkbey, et al., Multiparametric 3T prostate magnetic resonance imaging to detect cancer: histopathological correlation using prostatectomy specimens processed in customized magnetic resonance imaging-based molds. (2011), J Urol. 186(5):1818-1824.
Nelson, et al., Tissue geometry determines sites of mammary branching morphogenesis in organotypic cultures. (2006), Science 314(5797):298-300.
Bearer, et al., Multiparameter computational modeling of tumor invasion. (2009), Cancer Res 69(10):4493-4501.
Gallaher, et al., Bridging population and tissue scale tumor dynamics: a new paradigm for understanding differences in tumor growth and metastatic disease (2014), Cancer Res 74(2):426-435.
Lima, et al., A hybrid ten-species phase-field model of tumor growth. (2014), Mathematical Models and Methods in Applied Sciences 24(13):2569-2599.
Oden, et al., Toward predictive multiscale modeling of vascular tumor growth. Archives of Computational Methods in Engineering, (2015), doi:10.1007/s11831-015-9156-x.
Hawkings-Daarud, et al., Numerical simulation of a thermodynamically consistent four-species tumor growth model. (2012), Int J Numer Method Biomed Eng 28(1):3-24.
Qin, et al., Phase field method. Materials Science and Technology, (2010), 26(7):803-811.
Qin, et al., Phase-field model study of the crystal morphological evolution of hcp metals. (2009), Acta Materialia 57 (11):3382-3390.
Karma, et al., Unsteady crack motion and branching in a phase field model of brittle fracture. (2004), Phys Rev Lett 92(24):245510.
Gomez, et al., Three-dimensional simulation of unstable gravity-driven infiltration of water into a porous medium. Journal of Computational Physics, (2013), 238:217-239.
Bueno, et al., Interaction of complex fluids and solids: theory, algorithms and application to phase-change-driven implosion. (2015), Computational Mechanics 55(6): 1105-1118.
Gomez, et al., Isogeometric analysis of the Cahn-Hilliard phase-field model. Computer Methods in Applied Mechanics and Engineering, (2008), 197(49):4333-4352.

(56) References Cited

OTHER PUBLICATIONS

Vilanova, et al., Coupling of discrete random walks and continuous modeling for three-dimensional tumor-induced angiogenesis. (2014), Computational Mechanics 53(3):449-464.
Ciarletta, et al., The radial growth phase of malignant melanoma: multi-phase modelling, numerical simulations and linear stability analysis. (2011), J R Soc Interface 8(56):345-368.
Ellem, et al., The nature of conditioning nutrients for human malignant melanoma cultures. (1983), J Cell Sci 62 (1):249-266.
Cristini, et al., Nonlinear simulations of solid tumor growth using a mixture model: invasion and branching. (2009), J Math Biol 58(4-5):723-763.
Andasari, et al., Mathematical modeling of cancer cell invasion of tissue: biological insight from mathematical analysis and computational simulation. (2011), J Math Biol 63(1):141-171.
Sciume, et al., A multiphase model for three-dimensional tumor growth. (2013), New J Phys 15(1):015005.
Mueller-Klieser, et al., Influence of glucose and oxygen supply conditions on the oxygenation of multicellular spheroids. (1986), Br J Cancer 53(3):345-353.
Berges, et al., Implication of cell kinetic changes during the progression of human prostatic cancer. (1995), Clin Cancer Res 1(5):473-480.
Gerhardt, et al., VEGF guides angiogenic sprouting utilizing endothelial tip cell filopodia. (2003), J Cell Biol 161 (6):1163-1177.
Swanson, et al., A quantitative model for the dynamics of serum prostate-specific antigen as a marker for cancerous growth: an explanation for a medical anomaly. (2001), Am J Pathol 158(6):2195-2199.
Vollmer, Dissecting the dynamics of serum prostate-specific antigen. (2010), Am J Clin Pathol 133(2):187-193.
Vollmer, et al., Tumor volume in prostate cancer and serum prostate-specific antigen. Analysis from a kinetic viewpoint. (2003), Am J Clin Pathol 119(1):80-89.
Bosch, et al., Establishing normal reference ranges for prostate volume change with age in the population-based Krimpen-study: Prediction of future prostate volume in individual men. (2007), Prostate 67(16):1816-1824.
Richardson, et al., Age-specific reference ranges for serum prostate-specific antigen. (1997), Urol Clin North Am 24(2):339-351.
Lotan, et al., Clearance rates of total prostate specific antigen (PSA) after radical prostatectomy in African-Americans and Caucasians. (2002), Prostate Cancer Prostatic Dis 5(2):111-114.
Brandle, et al., Serum half-life time determination of free and total prostate-specific antigen following radical prostatectomy—a critical assessment. (1999), Urology 53(4):722-730.

\* cited by examiner

SIMULATION AND PATIENT-SPECIFIC SCALE TISSUE MODELLING OF THE GROWTH OF PROSTATE CANCER

BACKGROUND OF THE INVENTION

1. Field of the Invention

The invention generally relates to mathematical modeling and simulation of diseases and their treatments. More particularly, the invention relates to mathematical modeling and simulation of prostate cancer.

2. Description of the Relevant Art

According to the World Health Organization (WHO), prostate cancer (PCa) is the second most common cancer among men worldwide. In 2012, there was an estimate of 1,095,000 new cases and 308,000 deaths worldwide associated with this cancer. In 2016, PCa will be responsible for about 180,890 new cases and 26,120 deaths in the U.S.A.

In most cases, PCa is an adenocarcinoma, a form of cancer that originates and develops in epithelial tissues with glandular organization, for example, the prostatic tissue in charge of producing certain substances in semen. Adenocarcinomas arise as a result of genetic alterations in cell nuclei, such as mutations and epigenetic changes. Additionally, the influence of several environmental factors, such as diet, may promote further modifications of the genome. Tumoral cells exhibit an aberrant and competitive behavior, characterized by overproliferation and an invasive demeanor. Consequently, they may endanger the structure and the normal operation of the tissue they belong to, eventually jeopardizing the survival of the whole organism. The same tumor may present different groups of cancerous cells, with different metabolism, local environment and aggressiveness. Malignant cells may evolve during their life cycle, and thus belong to a new group. The structure, behavior and evolution of a tumor depend on the specific genetic alterations that may have originated it and supported its evolution.

The development of a prostate adenocarcinoma requires a gradual accumulation of mutations in a number of different genes, which varies from patient to patient, but is usually at least seven. As a result of these alterations of the genome over years, an initial moderate disorder of cell behavior evolves gradually towards an advanced cancer. As the tumor develops, it becomes more malignant and cell differentiation decreases. This evolutive phenomenon is called tumor progression and, in general, comprises four steps: (1) local overproliferation of cells, (2) extensive overproliferation of cells, (3) invasion of the surrounding tissues and, finally, (4) metastasis, which is the process whereby some malignant cells escape from the original tumor, enter the bloodstream and migrate to other tissue, which they invade and colonize.

Medical practice for PCa has been developed upon the above-mentioned genetic and biological bases as well as on the accumulated experience of physicians treating this disease. The current medical protocols include all these sources of knowledge on PCa in the form of statistics for the probability of cancer stage and treatment success. In brief, PCa is easier to cure in its early stages, before it becomes excessively aggressive and spreads out of the prostate but, unfortunately, this disease hardly ever produces any symptom until the tumor is either very large or has invaded other tissues.

Presently, the best way to combat PCa is a combination of prevention and regular screening for early detection. Regular screening for PCa usually consists of a Prostate Specific Antigen (PSA) test and a Digital Rectal Examination (DRE), which are usually performed periodically in men over age fifty. The PSA test is a blood test for measuring the serum level of this prostate activity biomarker, which rises during PCa. The DRE is a physical test in which the doctor palpates the rectal wall nearby the prostate searching for unusual firm masses, as healthy prostates are normally compliant. If either the DRE or the PSA test is positive, the patient will be asked to undergo a biopsy, an invasive procedure performed with a needle guided by transrectal ultrasound (TRUS), to obtain an average of 8 to 12 tissue cores. If cancerous cells are found in the biopsy, the structure and organization of the aberrant cells will be analyzed by a pathologist to determine the aggressiveness of the tumor, which is measured by a heuristic histopathological indicator known as the Gleason score. With the results of the DRE, the biopsy and some possible medical images, such as Magnetic Resonances (MRs) or Computed Tomographies (CTs), PCa guidelines are used to establish a clinical stage, that is, an estimation of how far cancer has progressed. Taking the clinical stage, PSA level and Gleason score together, protocols are utilized to define the risk group for a patient and associate a series of alternative treatments.

The selection of the treatment, such as surgery (radical prostatectomy), cryoablation, thermal ablation, high intensity focused ultrasound (HIFU), radiation therapy, hormonal therapy, chemotherapy or a combination of them, takes into account age, life expectancy, other aspects of the clinical history, and the personal preferences of individual patients. The chosen treatment may be of a curative or palliative nature, the former being the standard for localized PCa and the latter being the common practice for advanced PCa. In some cases, if the tumor is in its very early stages, or if the risk is judged to be very low, a curative treatment may be delayed while the patient is monitored until the appropriate moment for treatment (active surveillance). Patients that are not eligible for local curative treatment, or those with a short life expectancy, may benefit from a deferred palliative treatment, aimed at tackling specific symptoms of the disease, while they continue on regular screening (watchful waiting).

Biologists and physicians are actively engaged in the study of PCa in an attempt to shed light on the molecular, biological and physiological mechanisms that explain how tumors originate, grow and spread within the body. Despite the number of experimental and clinical investigations, a comprehensive theoretical model into which the abundance of data can be organized and understood is lacking.

SUMMARY

In one set of embodiments, a method of modeling the possible progression of prostate cancer in a subject may be implemented as follows.

The method includes performing operations on a computer system, wherein the operations include simulating evolution of a tumor in a prostate gland of the subject. The action of simulating is based at least on a coupled system of reaction-diffusion equations and a patient-specific geometric model of the prostate gland of the subject. The term "subject" and the term "patient" are used herein interchangeably.

In some embodiments, the patient-specific geometric model may be designed based on one or more medical images of the prostate gland of the subject.

In some embodiments, the patient-specific geometric model comprises a three-dimensional (or a two-dimensional) tensor-product spline. In these embodiments, the simulation may be performed in an isogeometric fashion.

In some embodiments, the simulation is performed according to a finite element method, or a finite difference method, or a finite volume method, or a mesh-free method, or an immersed method.

In some embodiments, the patient-specific geometric model is constructed based on any discretization method commonly used for constructing geometric models and/or solving partial differential equation mathematical models on geometric models.

In some embodiments, the reaction-diffusion equations include a first equation representing dynamics of a phase field $\phi$ and a second equation representing dynamics of a nutrient field $\sigma$. The value $\phi(x,t)$ of the phase field $\phi$ represents an extent to which cells at position x and time t are cancerous. The value $\sigma(x,t)$ of the nutrient field $\sigma$ represents a nutrient concentration at position x and time t.

In some embodiments, the simulation includes storing in memory an output dataset representing said evolution of the phase field $\phi$ and the nutrient field $\sigma$ on the geometric model over an interval in simulated time. The output data may be used to perform any of a wide variety of applications (or combinations of applications), as described herein.

In some embodiments, the operations performed by the computer system may also includes simulating evolution of a tissue PSA field p based at least on a third equation and said geometric model. The third equation may be of reaction-diffusion type, and include one or more of the following: a term that represents a rate at which healthy cells produce PSA; a term that represents a rate at which cancerous cells produce PSA; and a decay term that represents a natural decay of the tissue PSA. The tissue PSA field may be used to perform any of a variety of applications, as described herein.

In some embodiments, the operations also include: computing a boundary of the tumor based on a level set of the phase field; and displaying the boundary of the tumor via a display device.

BRIEF DESCRIPTION OF THE DRAWINGS

Advantages of the present invention will become apparent to those skilled in the art with the benefit of the following detailed description of embodiments and upon reference to the accompanying drawings.

Specific embodiments are shown by way of example in the drawings and will be described herein in detail. It should be understood, however, that the drawings and detailed description are not intended to limit the claims to the particular embodiments disclosed, even where only a single embodiment is described with respect to a particular feature. On the contrary, the intention is to cover all modifications, equivalents and alternatives that would be apparent to a person skilled in the art having the benefit of this disclosure. Examples of features provided in the disclosure are intended to be illustrative rather than restrictive unless stated otherwise.

The headings used herein are for organizational purposes only and are not meant to be used to limit the scope of the description. As used throughout this application, the word "may" is used in a permissive sense (i.e., meaning "having the potential to"), rather than the mandatory sense (i.e., meaning "must"). The words "include," "including," and "includes" indicate open-ended relationships and therefore mean "including, but not limited to". Similarly, the words "have," "having," and "has" also indicated open-ended relationships, and thus mean "having, but not limited to". The terms "first," "second," "third," and so forth as used herein are used as labels for nouns that they precede, and do not imply any type of ordering (e.g., spatial, temporal, logical, etc.) unless such an ordering is otherwise explicitly indicated. For example, a "third fastener coupled to a garment" does not preclude scenarios in which a "fourth fastener coupled to the garment" is connected prior to the third fastener, unless otherwise specified. Similarly, a "second" feature does not require that a "first" feature be implemented prior to the "second" feature, unless otherwise specified.

Various components may be described as "configured to" perform a task or tasks. In such contexts, "configured to" is a broad recitation generally meaning "having structure that" performs the task or tasks during operation. As such, the component can be configured to perform the task even when the component is not currently performing that task. In some contexts, "configured to" may be a broad recitation of structure generally meaning performs the task or tasks during operation. As such, the component can be configured to perform the task even when the component is not currently on.

Various components may be described as performing a task or tasks, for convenience in the description. Such descriptions should be interpreted as including the phrase "configured to." Reciting a component that is configured to perform one or more tasks is expressly intended not to invoke 35 U.S.C. § 112 paragraph (f), interpretation for that component.

The scope of the present disclosure includes any feature or combination of features disclosed herein (either explicitly or implicitly), or any generalization thereof, whether or not it mitigates any or all of the problems addressed herein. Accordingly, new claims may be formulated during prosecution of this application (or an application claiming priority thereto) to any such combination of features. In particular, with reference to the appended claims, features from dependent claims may be combined with those of the independent claims and features from respective independent claims may be combined in any appropriate manner and not merely in the specific combinations enumerated in the appended claims.

DETAILED DESCRIPTION OF THE PREFERRED EMBODIMENTS

It is to be understood the present invention is not limited to particular devices or methods, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise. Furthermore, the word "may" is used throughout this application in a permissive sense (i.e., having the potential to, being able to), not in a mandatory sense (i.e., must). The term "include," and derivations thereof, mean "including, but not limited to." The term "coupled" means directly or indirectly connected.

The following is a glossary of terms used in this disclosure:

Memory Medium—Any of various types of non-transitory memory devices or storage devices. The term "memory medium" is intended to include an installation medium, e.g., a CD-ROM, floppy disks, or tape device; a computer system memory or random access memory such as DRAM, DDR RAM, SRAM, EDO RAM, Rambus RAM, etc.; a non-volatile memory such as a Flash, magnetic media, e.g., a hard drive, or optical storage; registers, or other similar types of memory elements, etc. The memory medium may include other types of non-transitory memory as well or combinations thereof. In addition, the memory medium may be located in a first computer system in which the programs are executed, or may be located in a second different computer system which connects to the first computer system over a network, such as the Internet. In the latter instance, the second computer system may provide program instructions to the first computer for execution. The term "memory medium" may include two or more memory mediums which may reside in different locations, e.g., in different computer systems that are connected over a network. The memory medium may store program instructions (e.g., embodied as computer programs) that may be executed by one or more processors.

Carrier Medium—a memory medium as described above, as well as a physical transmission medium, such as a bus, network, and/or other physical transmission medium that conveys signals such as electrical, electromagnetic, or digital signals.

Computer System—any of various types of computing or processing systems, including a personal computer system (PC), mainframe computer system, workstation, network appliance, Internet appliance, personal digital assistant (PDA), television system, grid computing system, or other device or combinations of devices. In general, the term "computer system" can be broadly defined to encompass any device (or combination of devices) having at least one processor that executes instructions from a memory medium.

Processing Element—refers to various implementations of digital circuitry that perform a function in a computer system. Additionally, processing element may refer to various implementations of analog or mixed-signal (combination of analog and digital) circuitry that perform a function (or functions) in a computer or computer system. Processing elements include, for example, circuits such as an integrated circuit (IC), ASIC (Application Specific Integrated Circuit), portions or circuits of individual processor cores, entire processor cores, individual processors, programmable hardware devices such as a field programmable gate array (FPGA), and/or larger portions of systems that include multiple processors.

Automatically—refers to an action or operation performed by a computer system (e.g., software executed by the computer system) or device (e.g., circuitry, programmable hardware elements, ASICs, etc.), without user input directly specifying or performing the action or operation. Thus the term "automatically" is in contrast to an operation being manually performed or specified by the user, where the user provides input to directly perform the operation. An automatic procedure may be initiated by input provided by the user, but the subsequent actions that are performed "automatically" are not specified by the user, i.e., are not performed "manually", where the user specifies each action to perform. For example, a user filling out an electronic form by selecting each field and providing input specifying information (e.g., by typing information, selecting check boxes, radio selections, etc.) is filling out the form manually, even though the computer system must update the form in response to the user actions. The form may be automatically filled out by the computer system where the computer system (e.g., software executing on the computer system) analyzes the fields of the form and fills in the form without any user input specifying the answers to the fields. As indicated above, the user may invoke the automatic filling of the form, but is not involved in the actual filling of the form (e.g., the user is not manually specifying answers to fields but rather they are being automatically completed). The present specification provides various examples of operations being automatically performed in response to actions the user has taken.

Configured to—Various components may be described as "configured to" perform a task or tasks. In such contexts, "configured to" is a broad recitation generally meaning "having structure that" performs the task or tasks during operation. As such, the component can be configured to perform the task even when the component is not currently performing that task (e.g., a set of electrical conductors may be configured to electrically connect a module to another module, even when the two modules are not connected). In some contexts, "configured to" may be a broad recitation of structure generally meaning "having circuitry that" performs the task or tasks during operation. As such, the component can be configured to perform the task even when the component is not currently on. In general, the circuitry that forms the structure corresponding to "configured to" may include hardware circuits.

Various components may be described as performing a task or tasks, for convenience in the description. Such descriptions should be interpreted as including the phrase "configured to." Reciting a component that is configured to perform one or more tasks is expressly intended not to invoke 35 U.S.C. § 112, paragraph six, interpretation for that component.

Described herein is a phenomenological model for PCa that qualitatively reproduces in vitro experiments and the actual growth patterns of PCa during the early to mid-late stages of the disease, when PCa is usually diagnosed and treated. The computer simulations carried out with the described model suggest that prostate tumors may escape starvation and necrosis by developing a tubular shape or branching.

Although the potential of PSA as a PCa biomarker remains unclear, PCa diagnosis and monitoring in clinical practice relies heavily on PSA time evolution. Thus, in an embodiment, an equation that models the PSA dynamics within the prostatic tissue is described. Under certain assumptions, the integration of this equation leads to another equation that governs the dynamics of serum PSA, whose solution can be directly interpreted by a urologist.

In addition to the diagnosis and treatment of PCa, the PSA model can be used to investigate the role of PSA as a biomarker for PCa, which is currently one of the most contentious debates in the urology community. The herein described modeling and simulation technology also addresses new challenges posed by the tissue-scale problem. Traditional smaller-scale modeling usually ignores the geometry of the host tissue. Yet, experimental evidence shows that tissue geometry determines sites of branching morphogenesis and plays a key role in tissue growth, and, consequently, in cancer development. Accounting for tissue geometry is especially relevant in PCa because prostate anatomy varies significantly from one person to another, and PCa almost invariably develops in the peripheral zone of the prostate, close to the prostatic capsule. Thus, the combination of patient-specific anatomy and PCa modeling provides a model which is customized for the patient. In an embodiment, techniques of computational geometry are used to extract the precise anatomy of the prostate from medical images, as well as the initial location and shape of the tumor for a patient. Fully three-dimensional computer simulations are performed that predict the growth of the tumor, including the first patient-specific simulation of PCa evolution based on prostatic anatomy obtained from medical images.

In an embodiment, the possible progression of prostate cancer in a subject can be modeled by performing operations on a computer system, wherein the operations include: simulating evolution of a tumor in a prostate gland of a subject, wherein said simulating is based at least on a coupled system of reaction-diffusion equations and a geometric model of the prostate gland of the subject. The use of reaction-diffusion equations and a geometric model of the prostate gland of the subject provides a tumor growth model that predicts the expected progression of prostate cancer in the individual. The tumor growth model may be used to devise a customized treatment for the subject.

Most continuous mathematical models of tumor growth developed to date consider several tumor species and the host tissue as different interacting phases that compete in order to obtain nutrients, proliferate and occupy more space so as to thrive in the tumoral environment. Different malignant cell types are associated with different traits, such as whether the cells are alive or not (viable, necrotic), the oxygen concentration in their local environment (normoxic, hypoxic), and whether they exhibit a certain phenotype or acquired behavior due to genetic alterations (e.g., proliferative, invasive, resistance to a certain treatment). The dynamics of each cellular species is usually modeled with a diffusion-reaction equation. In some cases, convection is also accounted for, as well as other types of migration, for example, chemotaxis, that is, cell movement driven by gradients of dissolved substances in the cell environment, or haptotaxis, that is, cell movement driven by gradients of substances attached to the extracellular matrix. The dynamics of the nutrients, as well as any other substance with a major role in cancer progression, is included by means of additional diffusion-reaction equations.

The reaction-diffusion equations include a first equation representing dynamics of a phase field $\phi$ and a second equation representing dynamics of a nutrient field $\sigma$. In an embodiment, a value $\phi(x,t)$ of the phase field $\phi$ represents an extent to which cells at position x and time t are cancerous, wherein a value $\sigma(x,t)$ of the nutrient field $\sigma$ represents a nutrient concentration at position x and time t. The position x is a vector in two or three dimensions.

In the model presented herein, the phase-field method is used to account for the healthy-to-tumoral transition and the coupled dynamics of both the host tissue and the cancerous cells, resulting in the diffusion-reaction model in equation [1].

$$\frac{\partial \phi}{\partial t} = \lambda \Delta \phi - \frac{1}{\tau} \frac{dF(\phi)}{d\phi} + \chi \sigma - A\phi \qquad [1]$$

The parameter $\phi$ is a measure of cellular microstructure. This order parameter may vary between a lower limit and an upper limit, e.g., between 0 and 1, or between −1 and 1. Lower values represent healthy tissue while higher values represent an aberrant cell organization, typical of PCa. A boundary of the tumor corresponds to a level set (e.g., $\phi=0.5$) of the phase field.

The growth of PCa is driven by a host of hormones, growth factors, and vital nutrients, but for the sake of simplicity, it is assumed that tumor growth chiefly depends on nutrients, in particular, glucose. The model could also incorporate other substances, but their regulatory effect on PCa growth can be interpreted equivalently in terms of glucose. Hence, these ancillary substances affecting tumor growth can be accounted for by modifying the baseline glucose dynamics. Also, it is assumed that convection has a negligible contribution to the transport of glucose, a fact that is consistent with experimental observations. These assumptions lead to the diffusion-reaction model in equation [2].

$$\frac{\partial \sigma}{\partial t} = \epsilon \Delta \sigma + s - \delta \phi - \gamma \sigma \qquad [2]$$

In equation [1], $F(\phi)$ may be a double-well potential, a typical function within the phase-field method, that makes possible the stable coexistence of healthy and cancerous cells in the prostate. For example, $F(\phi)$ may take on the explicit form:

$$F(\phi)=16\phi^2(1-\phi)^2. \qquad [3]$$

The last two terms in equation [1] account for nutrient-driven growth and apoptosis (i.e., programmed cell death), respectively. It is assumed that the growth rate depends linearly on the local nutrient concentration with the growth rate coefficient $\chi$. The model further assumes that apoptosis follows a linear relation with the population of tumoral cells, A being its rate, as this is the natural response in the prostatic tissue. In equation [2], s is the nutrient supply. On the right-hand side of the equation, the third term represents the consumption of nutrient by the tumoral cells, while the fourth term accounts for the natural decay of nutrient.

The values for the model parameters can be obtained from studies on nutrient transport within tissues and tumor growth. In some embodiments, the following values are used for the parameters: $\tau=0.01$ year; $\delta=2.75$ g/(l·day); and $\gamma=1000$ l/year and are substantially constant. Several values are considered for the growth rate $\chi$ and the apoptosis rate A, ranging from $\chi=400$ l/(g·day) to $\chi=700$ l/(g·day) and from A=100 l/year to A=700 l/year, in order to recreate the different morphologies of PCa growth during its first stages. To make the problem computationally tractable, $\lambda \sim h^2/T$, where h is the characteristic length scale of the computational mesh and T is the characteristic time scale, which in some embodiments is considered to be 1 year. In accordance with other models of tumor growth, $\epsilon \sim 10\lambda$ to $\epsilon \sim 100\lambda$, which manifests the experimental observation that tumor dynamics is slower than nutrient dynamics.

Nutrient supply is introduced in two different fashions in order to simulate the experimental results regarding the tumor morphology change. Beginning with a homogeneous supply with a value $s_1=2.75$ g/(l·day), a series of simulations are preformed which show the shape instability that makes an initially rounded tiny mass of aberrant cells grow with a fingered pattern invading the surrounding tissue. Afterwards, the previous value is set to be the base $s_0$ upon which a mild heterogeneity c is added, where the heterogeneity takes values between −0.2 g/(l·day) and 0.2 g/(l·day). In this case the nutrient supply will be $s_2=s_0+c$. Making use of an experimental image, the heterogeneity c is determined according to the vascular network depicted in the image, so that the nutrient supply will be maximum, s=2.95 g/(l·day), near the blood vessels and minimum, s=2.55 g/(l·day), at a point sufficiently far from them. Both $s_1$ and $s_2$ attempt to represent in vitro conditions, but the latter aims at reproducing a more realistic scenario. However, for the tissue-scale, patient-specific simulations, a more appropriate constant value $s_3=2.70$ g/(l·day) is used.

An additional equation that models PSA dynamics within the prostate tissue is used, based on a novel measure for PSA: the tissue PSA p, or serum PSA concentration leaked to the bloodstream per unit volume of prostatic tissue. Hence, tissue PSA will allow us to study the spatial distribution of the sources of serum PSA concentration within the gland. Both healthy and cancerous cells secrete PSA, but the latter generally produce PSA at a much higher rate than healthy cells. Cancerous and healthy rates of PSA production per unit volume of prostatic tissue are designated by $\alpha_c$ and $\alpha_h$, respectively. Similarly to other substances within the prostate, such as the nutrient, it is assumed that the concentration of tissue PSA p diffuses over the prostatic tissue and decays naturally with a rate $\gamma_p$, following equation [4].

$$\frac{\partial p}{\partial t} = \eta \Delta p + \alpha_h(1-\phi) + \alpha_c \phi - \gamma_p p \quad [4]$$

Considering that p represents the concentration of serum PSA that leaks to the bloodstream per unit volume, then serum PSA $P_s$ can be defined as the integral of the tissue PSA p over the prostatic tissue $\Omega$, that is, $$P_s = \int_\Omega p \, d\Omega \quad [5]$$

If equation [4] is integrated over the tissue region that is being simulated and assuming free-flux boundary conditions, the following ordinary differential equation is obtained:

$$\frac{dP_s}{dt} = \alpha_h V_h + \alpha_c V_c - \gamma_p P_s \quad [6]$$

where $V_h$ and $V_c$ denote, respectively, the volumes of healthy and cancerous tissue. Using existing data of prostate gland volumes and age-related PSA scores for a cohort of healthy men, respectively, estimates of $\alpha_h$ and $\gamma_p$ were determined by means of equation [6], choosing the values $\alpha_h=6.25$ (ng/ml)/(cm³·year) and $\gamma_p=100$ l/year, respectively. Indeed, the value of $\gamma_p$ corresponds to a PSA half-life of 2.5 days, which is consistent with the accepted values. As PSA is produced in higher levels in cancerous cells, the first assumption was $\alpha_c=15\alpha_h$, yet this proportion can be modified to represent different real cases for each patient, also introducing different levels of PCa malignancy. Finally, as both cancerous cells and a higher production of PSA are linked features in PCa, it is assumed that $\eta=\lambda$.

Taking into account PSA dynamics, the action of simulating evolution of a tissue PSA field p may be based at least on a third equation (such as equation [4]) and said geometric model of the prostate gland of the subject, wherein the third equation is of reaction-diffusion type, where the third equation includes one or more of the following: a term that represents a rate at which healthy cells produce PSA; a term that represents a rate at which cancerous cells produce PSA; a decay term that represents a natural decay of the tissue PSA. Specifically, the third equation may include one or more of the following: a term that is proportional to 1−ϕ (i.e., one minus the phase field ϕ); a term that is proportional to the phase field ϕ; a term that is proportional to the negative of the tissue PSA field.

If PSA dynamics are incorporated into the tumor growth model, the tumor growth model can be used to compute an evolution of serum PSA by numerically integrating the tissue PSA field over a volume of the patient-specific geometric model. The results may be presented by displaying a graph of the evolution of the serum PSA via a display device. In an embodiment, the image of the tissue PSA field may be displayed along a cross section of the patient-specific geometric model (e.g., a user specified cross section), wherein the cross section passes through at least a portion of the tumor. In some embodiments, a video of the evolution of the tissue PSA field on a cross section through the patient-specific geometric model may be displayed, wherein the cross section passes through at least a portion of the tumor.

Numerical Analysis and Simulations

Any of a wide variety of methods may be used to numerically solve the set of equations that define the tumor growth model, e.g., a finite element method, or a finite difference method, or a finite volume method, or any of various mesh-free methods, or any of various immersed methods. The nonlinearity of the set of equations and the complex geometry of both the prostate and the initial tumor in the patient-specific simulations demand efficient methods of resolution in terms of memory and time of computation. In some embodiments, to perform the numerical simulations, algorithms based on the concept of Isogeometric Analysis (IGA) may be employed. IGA is an emergent and cutting-edge technology that can be seen as a generalization of finite element analysis. In IGA, the standard piecewise polynomials used in the finite element method are replaced with richer functions used in computer graphics and computational geometry, such as, for example, B-Splines, Non-Uniform Rational B-Splines (NURBS) and T-Splines. To speed up the calculations and create a technology that facilitates obtaining solutions in a clinically relevant time, dynamic mesh-adaptivity techniques may be employed, e.g., techniques based on the concept of hierarchical refinement and coarsening, which enables the adaptation of the computational mesh dynamically throughout the simulation such that the approximation functions are richer close to the tumor surface, leading to dramatic savings of memory and compute time.

In an embodiment, a patient-specific geometric model of the prostate gland of the subject is designed based on one or more medical images of the prostate gland of the subject (e.g., images such as X-Ray images, CT images, MRI images, ultrasound images, or any combination of the foregoing). The patient-specific geometric model may include a three-dimensional tensor-product spline (such as a B-Spline, or a Non-Uniform Rational B-Spline, or a T-Spline). The locations of model space control points of the tensor-product spline may be specified by a set of user inputs. (For example, the set of user inputs may be received by a computer-aided design (CAD) program executing on a computer system.) The locations of the control points may be specified so that the spline conforms to the subject's prostate gland, as represented in the one or more medical images. The locations of the control points may be specified prior to simulating the evolution of a tumor in a prostate gland. In a further embodiment, the simulation of the evolution of a tumor in the prostate gland is performed in an isogeometric fashion, i.e., using geometric basis functions of the geometric model as analysis basis functions for said simulating.

More generally, the patient-specific geometric model of the prostate gland may be constructed based on any discretization method, e.g., any discretization method known (or commonly used) for solving partial differential equation mathematical models on geometric models.

To extract geometric models of the prostate and the initial tumor, several methods may be used to construct solid anatomic NURBS models. Since the geometry of a prostate is topologically equivalent to that of a torus, a parametric mapping method may be used to deform a torus NURBS model to match with the patient-specific prostate surface obtained from CT data, as depicted in FIGS. 1A-D. (NURBS is an acronym for Non-Uniform Rational B-Spline.) Finally, the computational mesh can be hierarchically refined so that it will represent the anatomy of the prostate to perform precise patient-specific simulations.

Figure 1A:
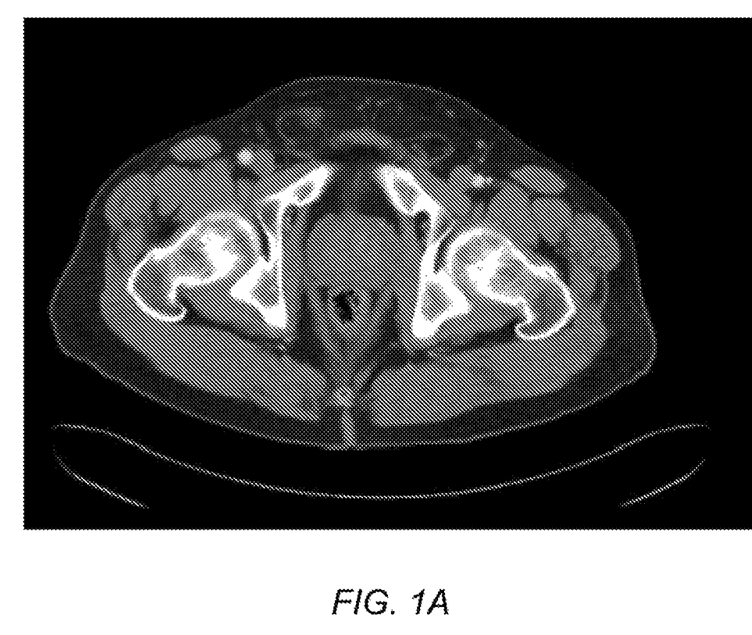
FIGS. 1A-D depict the extraction of the geometry of the prostate and initial tumor from CT data of the patient, according to some embodiments.
Figure 1B:
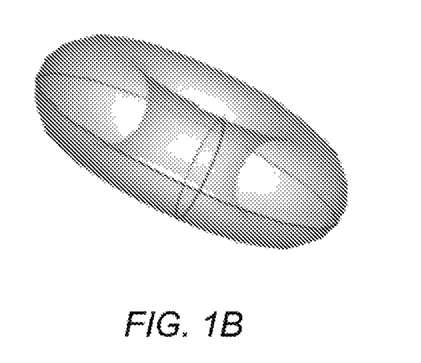
Figure 1C:
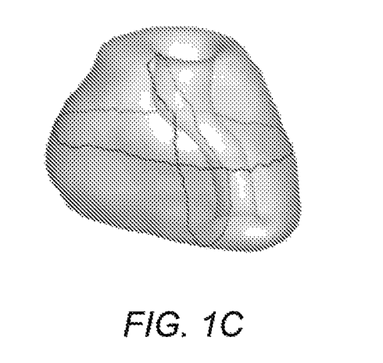
Figure 1D:
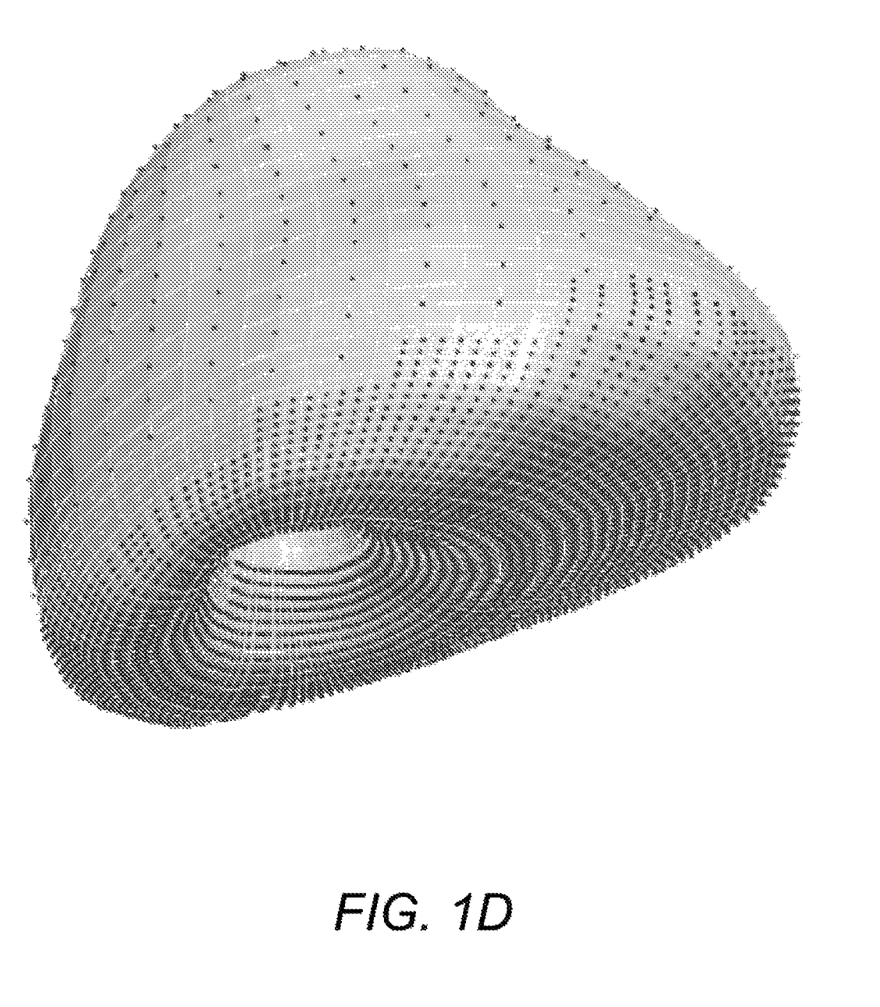

FIGS. 1A-D depict the extraction of the geometry of the prostate and the initial tumor from CT data. The process to perform tissue-scale, patient-specific simulations may begin by extracting in vivo data of the patient from medical images, such as his prostate anatomy, the tumor location and its shape. FIG. 1A depicts an axial CT image of the patient's abdomen at the height of the middle prostatic gland. As illustrated in FIG. 1B, a NURBS model of a torus is generated. The torus is topologically identical to a prostate. In FIG. 1C, the torus is mapped using computer graphics techniques to the actual geometry of the patient's prostate (posterior view). Finally, in FIG. 1D, hierarchical refinement is used to generate the computational mesh (anterior view).

In some embodiments, CT imaging may not be sufficiently accurate to detect localized PCa. Thus, multiparametric MM data may be used to get the location and estimated shape of the tumor. Alternatively, in order to introduce the initial tumor in the prostate model, the tumor geometry may be approximated as an ellipsoid. In particular, a three-dimensional field (e.g., a hyperbolic tangent function, an inverse tangent function, or any function with similar mathematical properties) may be $L^2$-projected onto the spline space that defines the anatomy of the patient's prostate in order to approximate the initial tumor with the phase field, hence obtaining an ellipsoidal cancerous mass in terms of the order parameter $\phi$ (see FIG. 3A).

Growth Patterns of Localized PCa

The morphology of PCa may vary from spheroidal tumors to tubular or fingered structures that invade the prostatic epithelium forming branches, as demonstrated by clinical practice and in vitro experimental studies involving cultures of prostate epithelial cells. Large-scale, two-dimensional and three-dimensional simulations of equations [1] and [2] show that the model can predict both growth types (spherical and fingered), as depicted in FIGS. 2A-F. Thus, the model qualitatively reproduces the associated clinical and experimental results for both morphologies.

Figure 2A:
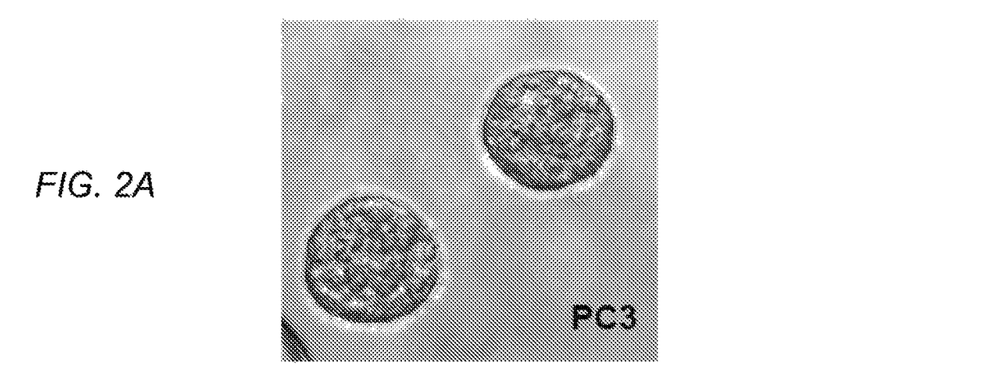
FIGS. 2A-F illustrate different growth morphologies adopted by initially spheroidal prostatic tumors, according to some embodiments.
Figure 2B:
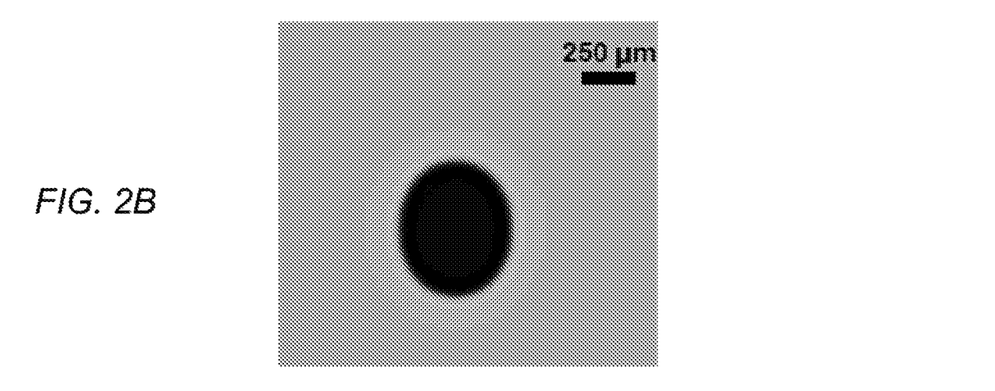
Figure 2C:
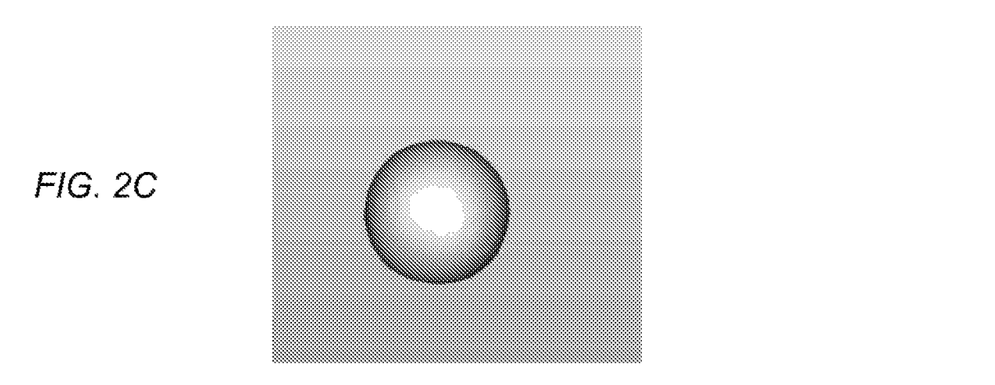
Figure 2D:
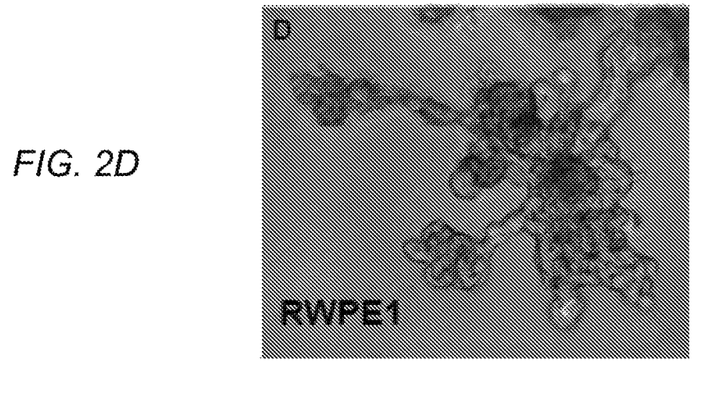
Figure 2E:
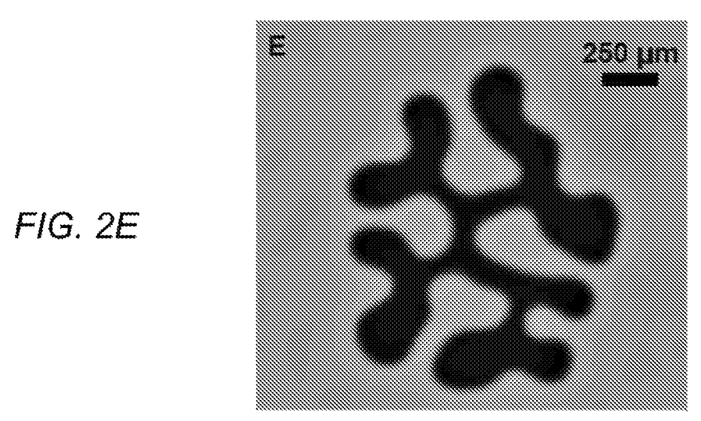
Figure 2F:
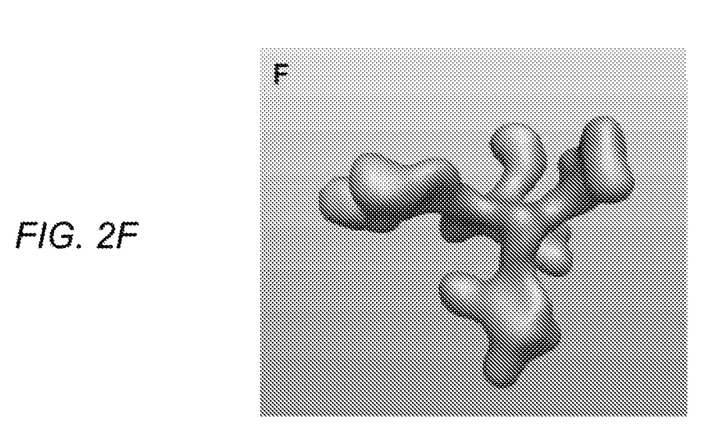

FIGS. 2A-F illustrate different growth morphologies adopted by initially spheroidal prostatic tumors. Large-scale, two-dimensional and three-dimensional simulations of the model reproduce the spheroidal and fingered tumor growth patterns as seen in clinical practice and experiments ($\lambda=5 \cdot 10^{-11}$ cm$^2$/s, $\epsilon=2 \cdot 10^{-9}$ cm$^2$/s). The heterogeneous nutrient supply $s_2$ was used in these simulations to produce more realistic patterns of growth. FIG. 2A depicts in vitro three dimensional Matrigel culture of PC-3 cells growing with a spherical or rounded pattern. Large-scale, two-dimensional (FIG. 2B) and three-dimensional (FIG. 2C) simulations of the model reproducing spheroidal growth ($\chi=400$ l/(g·year), A=300 l/year) are shown. FIG. 2D depicts in vitro three dimensional Matrigel culture of RWPE-1 cells showing a fingered morphology. Large-scale, two-dimensional (FIG. 2E) and three-dimensional (FIG. 2F) simulations of the model reproducing fingered growth ($\chi=600$ l/(g·year), A=600 l/year) are shown.

It has been suggested that this change in tumor morphology is promoted by a series of chemical signals, also motivated by specific mutations or epigenetic changes. However, a conclusive explanation of the mechanisms of this shift in cancer growth remains largely unknown. Shape instability was activated using two mechanisms previously suggested in the literature: first, increasing the parameters $\chi$ and A in equation [1], which represents a more aggressive cancer with larger apoptosis, and second, reducing the value of the nutrient supply s, which may be understood as a situation in which the tumor is surrounded by a harsh microenvironment.

Spheroidal or ellipsoidal growth takes place in the very first stages of PCa, when it is not excessively malignant. At these early stages the tumor will feature low values for the growth rate $\chi$ and the apoptosis rate A. In particular, taking the aforementioned default values for all the parameters in the model, $\chi=400$ l/(g·year) and A=300 l/year, leads to a spheroidal pattern of growth, as can be seen in FIGS. 2B and 2C. Conversely, the fingered morphology corresponds to a more advanced cancer in comparison to the spheroidal pattern, still within the scope of localized PCa. This tubular growth can be reproduced by the model with higher values of these two parameters, which may also be balanced, that is, they may take similar values. In order to perform the simulations depicted in FIGS. 2E-F, the following assumptions were made $\chi=600$ l/(g·year) and A=600 l/year, which appear to yield a characteristic fingered morphology.

Interestingly, with this latter selection of parameters spheroidal growth was initially observed. Should the tumor continue to develop with this morphology, the nutrient concentration in its central region would drop to values promoting hypoxia, starvation and necrosis. However, once the tumor reaches a volume that would lead to this inner harmful environment, the shift towards the fingered morphology takes place. With this growth pattern, the nutrient concentration within the tumor is not critical any longer. Regardless of whether the homogeneous or the heterogeneous definition for the nutrient supply is used, as long as $s_1=s_0$, the shape instability will occur at a similar time. However, the spatial distribution will be different, as the homogeneous nutrient supply produces symmetrical patterns of fingered growth and the introduction of a mild heterogeneity promotes growth along the gradients of $\sigma$.

If the value of the nutrient supply is reduced, that is, $s_1$ for the homogeneous version, and so for the heterogeneous one, then fingered growth may take place for a selection of $\chi$ and A which would produce spheroidal growth otherwise. Furthermore, in the range of values for $\chi$ and A typical of fingered growth, reducing s accelerates the onset of the shape instability. It was also observed that a drop in the values of s leads to slower tumor growth, while increasing the nutrient supply makes the tumor grow at a faster rate. In the case of the fingered morphology, the higher the value of s, the thicker the branches of the tumor, as the resulting higher concentrations of the nutrient within the tissue support larger tumor structures.

In some embodiments, simulating the evolution of a tumor in a prostate gland includes storing in memory an output dataset representing said evolution of the phase field φ and the nutrient field σ on the patient-specific geometric model over an interval in simulated time. The output dataset may be used in many different ways, e.g., to study tumor progression.

In one embodiment, the output dataset may be used to estimate a real-world time (e.g., a calendar date) at which one or more of the following tumor events may occur:

(1) the tumor will penetrate a capsule of the prostate gland of the subject;

(2) the tumor will invade a tissue outside (or near) the prostate gland of the subject;

(3) the tumor will reach a specified part of the prostate gland of the subject;

(4) the tumor will transition from ellipsoidal growth to fingered growth; and (5) the tumor will make contact with the urethra of the subject.

The real-world time or an indication of the real-world time may be outputted, e.g., to a healthcare professional, via an output device (such as a display device or speaker).

In one embodiment, a video may be generated based on at least a portion of the output dataset, wherein the video illustrates evolution of a boundary of the tumor over time. The video may be outputted, e.g., to a healthcare professional, via an output device (such as a display device).

In one embodiment, an image dataset may be generated based on the output. The image may illustrate a cross section through the patient-specific geometric model and include one or more curves corresponding to (or representing) a boundary of the tumor. The image may be outputted, e.g., to a healthcare professional, via an output device (such as a display device).

In one embodiment, a 3D rendering of the prostate gland and the tumor may be generated (e.g., using the techniques of 3D computer graphics) based at least on the output data set and the patient-specific geometric model. The 3D rendering may be outputted, e.g., to a healthcare professional, via an output device (such as a display device).

In one embodiment, an estimate of a stage of prostate cancer development in the subject may be generated based on the output dataset and multiparametric MRI data of the prostate gland of the subject. For example, the estimate may be determined based on a correlation between a tumor boundary in the multiparametric MRI image data and a tumor boundary derived from the output dataset. The estimated stage of prostate cancer development may be outputted, e.g., to a healthcare professional, via an output device (such as a display device).

In one embodiment, the output data set may be used to compute a boundary of the tumor based on a level set of the phase field. The computed boundary of the tumor may be outputted, e.g., to a healthcare professional, via an output device (such as a display device). In some embodiments, the volume of the tumor may be determined based on the computed boundary. An indication (e.g., a numerical value or a graph) of the computed volume may be outputted, e.g., to a healthcare professional, via an output device (such as a display device). In some embodiments, a three-dimensional field (e.g., a hyperbolic tangent function or any function with similar mathematical properties) may projected onto a model space corresponding to the geometric model, to approximate the initial tumor with the phase field.

In one embodiment, a health risk (such as prostatic capsule penetration, invasion of nearby tissues or tumoral expansion to different parts of the prostate gland) associated with growth of the tumor in the subject may be predicted based on the output dataset. The health risk determination may be outputted, e.g., to a healthcare professional, via an output device (such as a display device).

In one embodiment, a likelihood (or expected time of occurrence) of an adverse symptom (such as impotence or irregularity in urination and/or ejaculation) associated with growth of the tumor in the subject may be predicted based on the output dataset. An indication of the likelihood (or the expected time of occurrence) of the adverse symptom may be outputted, e.g., to a healthcare professional, via an output device (such as a display device).

In one embodiment, a type of prostate cancer treatment (e.g., chemotherapy, radiation, surgery, high intensity focused ultrasound (HIFU), hormonal therapy, etc.) for the subject may be selected based on the output dataset. An indication of the selected type may be outputted via an output device (e.g., displayed via a display device), e.g., to a healthcare professional.

In one embodiment, a time to start prostate cancer treatment on the subject may be selected based on the output dataset. An indication of the selected time may be outputted via an output device (e.g., displayed via a display device), e.g., to a healthcare professional.

In one embodiment, an anticancer drug or hormone to be administered to the subject may be selected based on the output dataset. An indication of the selected drug or hormone may be outputted via an output device (e.g., displayed via a display device), e.g., to a healthcare professional.

In one embodiment, a session of radiation treatment in order to radiatively kill cells in at least a portion of the tumor may be planned based on the output dataset. For example, a trajectory of beam direction and intensity for a radiation beam may be determined based on the output dataset. A plan for the session may be outputted via an output device (e.g., displayed via a display device).

In one embodiment, a chemotherapy treatment may be planned based on the output dataset, in order to increase the effectiveness of the treatment. A chemotherapy treatment plan may be outputted via an output device (e.g., displayed via a display device).

In one embodiment, a session of high intensity focused ultrasound (HIFU) may be planned based on the output dataset, in order to kill cells in at least a portion of the tumor. A plan for the HIFU session may be outputted via an output device (e.g., displayed via a display device).

In one embodiment, a session of surgery may be planned based on the output dataset, e.g., surgery to remove at least a portion of the tumor. A surgery plan may be outputted via an output device (e.g., displayed via a display device), e.g., to a health professional. The surgery plan may include, e.g., a specification of a series of surgical incisions.

In one embodiment, a robotic surgical tool (e.g., scalpel) may be controlled based on the output dataset, in order to remove at least a portion of the tumor.

In one embodiment, the output dataset may be used to determine invasive pathways for sampling and/or administration of therapeutic agents. For example, an insertion path of a biopsy needle may be determined based on the output data set, in order to increase a likelihood of obtaining samples of tumor tissue. An insertion path of a syringe may be determined based on the output dataset in order to inject cancer killing chemicals into at least a portion of the tumor. An insertion path of a syringe may be determined based on the output dataset in order to sample fluid and/or cells from at least a portion of the tumor. The proposed invasive pathway may be outputted, e.g., to a healthcare professional, via an output device (such as a display device).

The phrase "outputting via an output device" may take various forms in various embodiments. In some embodiments, the output device may include a display device, in which case the action of "outputting" includes displaying via the display device. In other embodiments, the output device may include a speaker, in which case the action of "outputting" includes outputting an audio signal via the speaker. In other embodiments, the output device may include a transmitter, in which case the action of "outputting" includes transmission of a signal (or information) over a transmission medium, e.g., a wireless medium or a wired medium. For example, the outputting may include transmission of information over the Internet or other computer network. In some embodiments, the output device may include a 3D printer, in which case the action of "outputting" includes sending information to the 3D printer in order to print a 3D object, e.g., an object representing the tumor (or the prostate gland including the tumor).

EXAMPLES

Patient-Specific Simulation

The Austin Radiological Association provided us with a series of axial and coronal CT images of a small cohort of patients with PCa, with and without contrast. CT is a not a suitable technique for the detection of localized PCa due to its reduced contrast between healthy and cancerous tissue within this gland. However, it is implemented in PCa protocols primarily in order to scan for metastasis or as a resource to initially analyze the prostate anatomy and the pelvic region with more detail than ultrasound.

Figure 3:
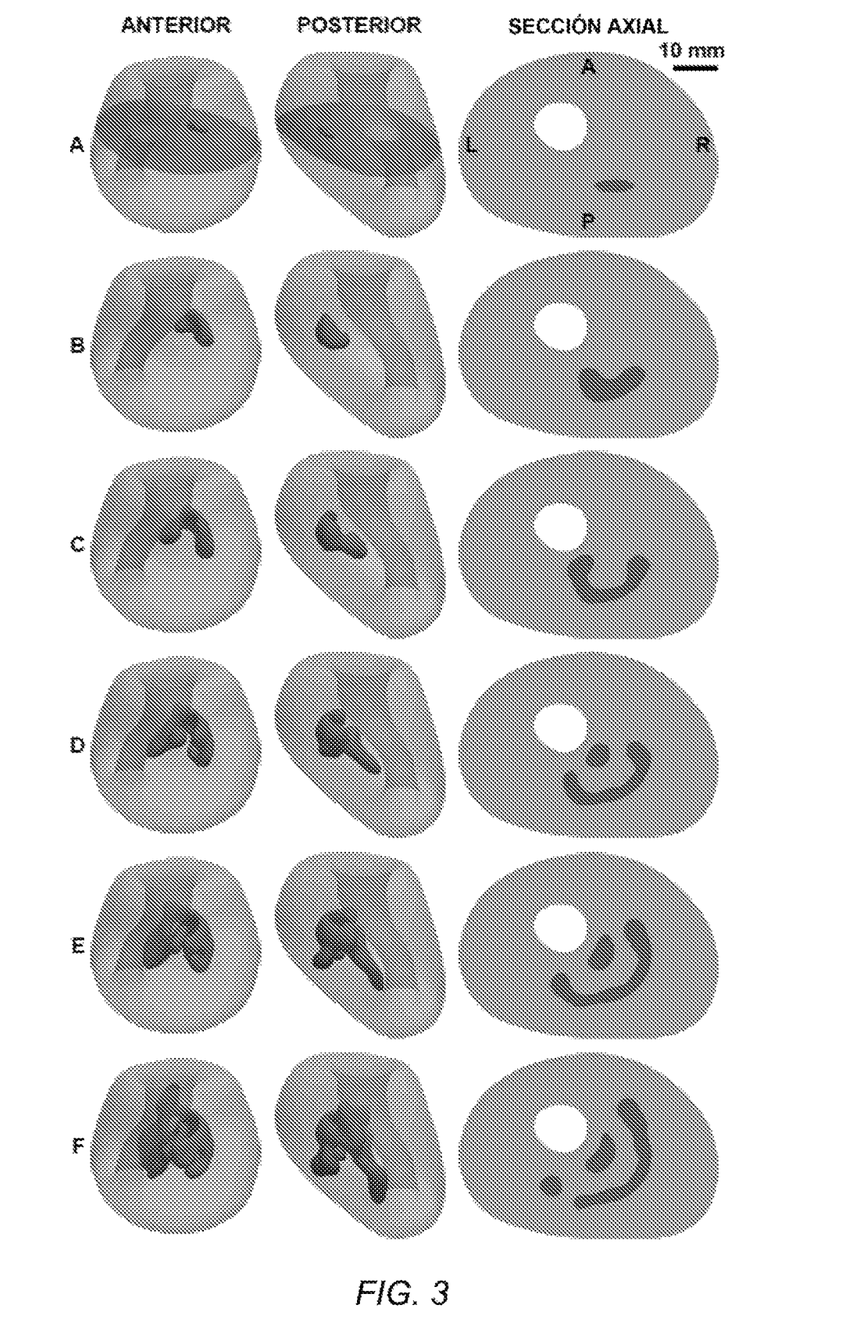
FIGS. 3A-F illustrate the prediction of growth of a prostatic adenocarcinoma at tissue scale, according to one embodiment of the computational model and on a patient-specific basis.

A patient was chosen in order to predict the evolution of his prostatic tumor using the model described herein and assess the performance of the simulation on the basis of the current knowledge of PCa evolution. This patient showed a small cancerous lesion of 0.03 cm$^3$, previously detected by ultrasound, in the posterior part of the peripheral zone at the middle region of the prostatic gland. The volume of the prostate gland is considered constant along the simulation and has a value of 71.67 cm$^3$. FIGS. 3A-F represent the prediction of the growth of a prostatic adenocarcinoma according to the model at tissue scale and on a patient-specific basis. As shown in FIGS. 3A-F, the model was run on the actual geometry of the prostate of the patient under consideration, after extracting it and the initial tumoral volume from the CT output files. These images show the predicted evolution of a prostatic tumor on the actual anatomy of the prostate of an individual patient ($\chi$=0.24 mm$^2$/day, $\epsilon$=7.5 mm$^2$/day). The axial section depicted is at z=25.5 mm, with the origin of the coordinate z set at the prostate base (A: anterior, P: posterior, L: patient's left, R: patient's right). The position of this section has been shaded in the anterior and posterior views for t=0. FIG. 3A depicts the initial tumor as identified in the patient's CT images. FIGS. 3B-F depict predicted growth according to the model during 1 year, with each sub figure corresponding to a time of 0.2 years apart.

This simulation represents tumor growth during 1 year and at the end the tumor volume is 2.66 cm$^3$. Initially, the tumor grows following an ellipsoidal pattern but it soon starts to develop preferential directions of growth, defining finger-like structures. As the tumor expands within the prostate, its geometry evolves toward a structure consisting of thickened layers of cancerous tissue with fingered protrusions along the main directions of growth. The axial section at the mid-gland shows an evolution from the spheroidal pattern of growth to the fingered morphology similar to that observed in large-scale, 2D and 3D simulations. The tumoral area in these sections qualitatively matches some delineations of PCa made on actual histopathologic specimens.

Tissue and Serum PSA

In the simulations, tissue PSA evolution is obtained from equation [4], and serum PSA evolution is then obtained from equation [6]. The field of tissue PSA typically shows higher values in the central areas of the tumor and lower values further away from the lesion, as depicted in FIGS. 4A-F. The difference in the values of p in healthy and cancerous tissue is due to the fact that the initial tumor starts producing PSA at a higher rate from the first moment and, as the tumor grows, higher tissue PSA values are found in the areas occupied by cancerous cells and following the preferential directions of growth. In general, tissue PSA values do not differ greatly between healthy and tumoral tissue in the model's 2D and 3D experimental simulations. However, in the tissue-scale, patient-specific simulations, the values of p in the tumor, around 0.70 (ng/ml)/cm$^3$, were an average of 3 times higher than in the healthy regions, around 0.24 (ng/ml)/cm$^3$, as seen in FIGS. 4A-F.

Taking lower values for $\alpha_c$, but greater than $\alpha_h$, the field of tissue PSA becomes more homogeneous, meaning that the peak values are lower too, due to the reduced difference between the rates of production of PSA in healthy and cancerous cells. The evolution of serum PSA is linked to the velocity of tumor growth. The faster the tumor grows, the faster serum PSA increases because there are more tumoral cells, producing PSA at a higher rate. Taking lower values for $\alpha_c$ also induces lower PSA scores in blood and the PSA velocity is also slowed down.

The serum PSA is obtained by integrating the values of p over the entire prostate anatomy. Since the biochemical data for the patients was not available, the baseline serum PSA was estimated according to the tumor stage and the dynamics imposed by the model. Beginning with the minimum value of 4.0 ng/ml, beyond which a physician would recommend a TRUS-guided biopsy, a steep jump towards a higher value was observed in the first time steps and then serum PSA followed exponential dynamics, as observed in clinical practice. Therefore, in order to produce more realistic simulations, the model was restarted once this readjustment of serum PSA was completed, correcting the initial condition for p so that it corresponded to the value of serum PSA reached just after the rising branch. Hence, serum PSA readjustment was eliminated and it followed exponential dynamics from the beginning of the simulations. In particular, an initial serum PSA level of 17.3 ng/ml was estimated and, at the end of the simulation, PSA reaches 18.9 ng/ml.

Figure 4:
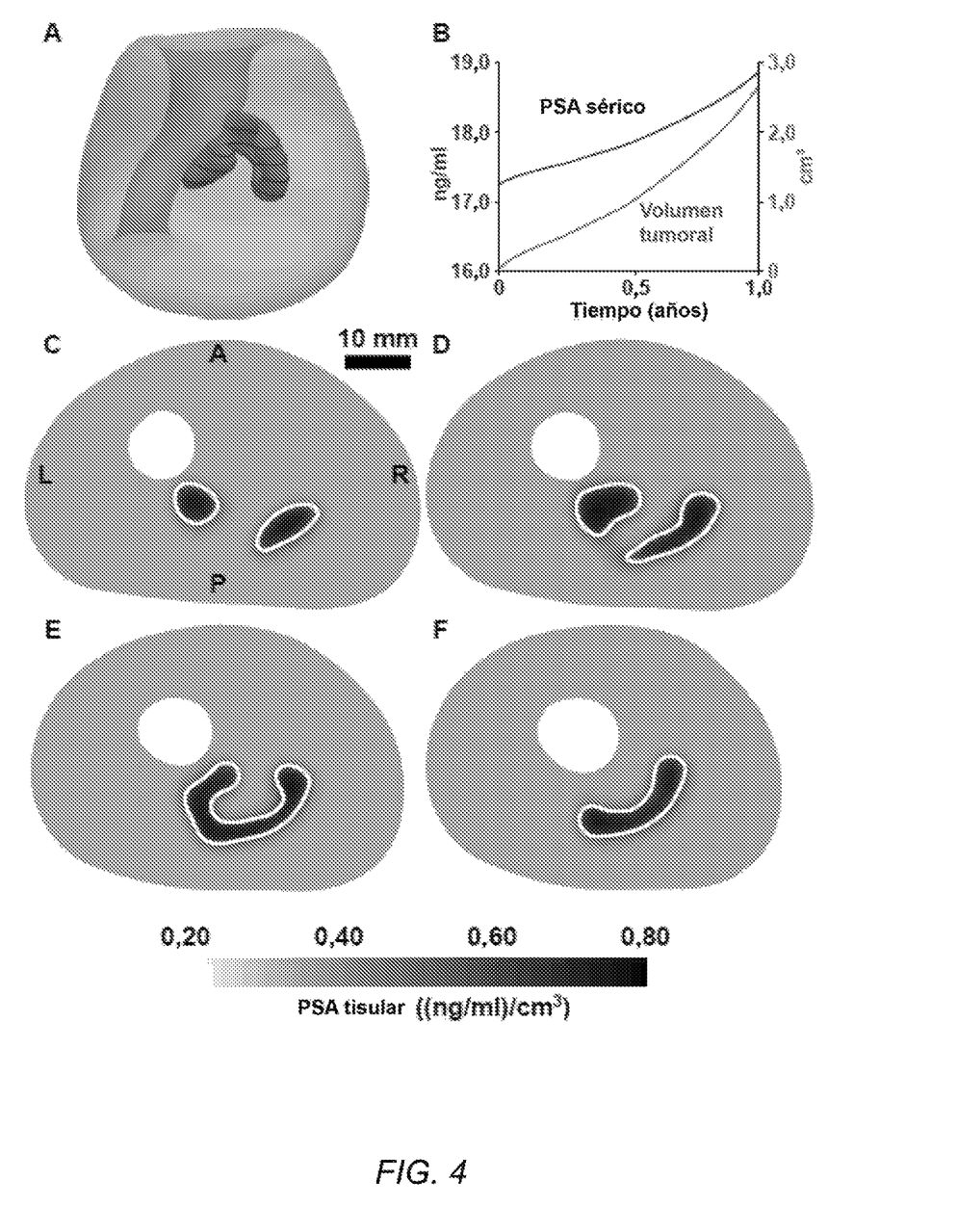
FIGS. 4A-F illustrate tissue PSA distribution across the prostate gland at a particular value of simulation time as well as tumor volume evolution and serum PSA history, according to some embodiments.

In FIGS. 4A-F, tissue PSA distribution across the prostate gland at t=0.5 years, tumor volume evolution and serum PSA history are depicted. Tissue PSA takes higher values on the tumoral tissue because it is produced by cancerous cells at a higher rate. FIG. 4A depicts an anterior view of the prostate and tumor at t=0.5 years with the location of the axial sections depicted in this figure as black contours on the tumor. FIG. 4B depicts predicted serum PSA and tumor volume time histories. FIGS. 4C-F depict evenly-spaced axial sections of the prostate representing the distribution of tissue PSA p at time t=0.5 years and height z=18.3 mm, z=21.6 mm, z=24.9 mm, and z=28.2 mm, respectively, with the origin of the coordinate z set at the prostate base. The white line is the contour of the tumor (A: anterior, P: posterior, L: patient's left, R: patient's right).

Predictive medicine and mathematical oncology offer a cutting-edge approach to medical practice. These new trends may be the key to organize and broaden the understanding of some critical diseases nowadays, such as PCa, by providing robust, comprehensive theoretical models integrating all the major known and forthcoming results from research in biological, biophysical, medical and biomedical sciences as well as engineering and computational mechanics. In particular, the simple model presented herein is able to reproduce the typical features of prostatic adenocarcinoma growth during the first to mid-late stages of this disease as seen in experimental results and clinical practice. This model may be implemented in clinical software for physicians to aid in the diagnosis of the disease, the prediction of its evolution, assessment of alternative treatments, and management of follow-up.

Tissue-Scale, Patient-Specific Simulations

Patient-specific simulations (see FIGS. 3A-F) were carried out over the actual anatomy of a patient, introducing the tumor morphology at the time of diagnosis by extracting both geometries from CT output data. It was observed that if the position of the tumor was changed within the prostate, but conserved its original shape, the tumoral pattern of growth was different. These results suggest that cancer growth morphology is dependent on the particular geometry of the tumor as well as on the specific anatomy of the prostate. Consequently, this observation supports the major importance of considering patient-specific anatomies for both the prostate and the tumor to accurately predict tumor growth. Introducing the particular anatomy of a patient in the model is crucial in order to predict the potential risks that PCa growth may entail, such as prostatic capsule penetration, invasion of nearby tissues or tumoral expansion to the different parts of the prostate, hence triggering symptoms such as impotence or irregularities in urination and ejaculation.

The possibility to predict when these risks or symptoms will appear would be a major advance in watchful waiting and active surveillance. Hence, the optimization of these two clinical options to manage the disease, including the modeling and simulation of PCa, would decrease the overtreatment of patients, in many instances leaving them relieved or cured after the delivery of the corresponding treatment, with minimum side effects and a good quality of life. The inclusion of the individual's prostate and tumor geometries is important in order to adequately follow up the progression of the disease in terms of tumor volume and location and PSA production, both before and after the delivery of a certain treatment. Predicting the actual tumor shape and volume within the anatomy of the prostate of a given patient would enable optimization of surgery and radiation therapy planning and delivery, obtaining high precision and efficiency rates.

The simulation presented in FIGS. 3A-F shows an important and typical feature of PCa, namely, why some biopsies are falsely negative or apparently yield a lower tumoral stage. As the tumor grows, it develops finger-like structures after the morphology shift that, in a three-dimensional, patient-specific scenario, evolve not only as branches but also as thickened layers of cancerous cells. Likewise, there are other layers and regions of healthy tissue surrounding and in between these cancerous layers, which are required in order to provide an adequate distribution of the nutrient. When a biopsy is performed following the current standards, a number of tissue samples are obtained in prescribed positions trying to map the whole prostatic gland. However, the tumor might be out of the reach of the needle used in the biopsy, resulting in a false negative, or it may target one of these tumoral thickened layers orthogonally, what may produce a low percentage of tumor in the tissue sample, leading to further biopsies or/and an erroneous stage of PCa that may compromise the patient quality of life and survival. One might conclude that the pathology analysis of a prostatic tumor biopsy would always provide a lower bound to the severity of the cancer, creating a dangerous predictive scenario.

Ideally, the combination of multiparametric MM and computational modeling and simulation of PCa may eliminate the biopsy of the prostate during PCa diagnosis and staging, hence dropping an invasive procedure with questionable outcomes and under continuous debate in the medical community. In fact, the combination of T2-weighted MRI, diffusion-weighted MRI, dynamic contrast-enhanced MRI and, optionally, magnetic resonance spectroscopic imaging, has already been able to detect and stage PCa with high sensitivity and specificity, comparable to those of current standard biopsies. As a result, multiparametric MM is now increasingly regarded as a future option to biopsy or, at least, a technique to be fused to TRUS-guided biopsy in order to optimize this procedure.

Modeling and Simulation of PSA Kinetics

An equation to model the behavior of PSA may also be added by introducing a novel measure, tissue PSA or the serum PSA concentration leaked to the bloodstream per unit volume of prostate tissue, equation [4]. This can be integrated over the computational domain that represents the anatomy of the prostate, allowing serum PSA dynamics to be followed as shown in equation [6]. The tissue PSA allows where PSA is being leaked to the bloodstream to be analyzed and the amount of this PCa biomarker discharged by each type of tissue, as depicted in FIGS. 4A-F. Furthermore, the results presented in FIGS. 4A-F also show that the model is able to compute a realistic evolution for serum PSA, similar to those seen in the literature. Tissue PSA links serum PSA to tumor burden in the model, hence establishing a theoretical basis for the link between both dynamics. A corroboration of this connection arose when the baseline serum PSA was estimated for the simulation. For a given selection of parameters in equations [1] and [4], and the initial tumoral volume, the initial serum PSA was intrinsically determined. Therefore, if the simulation begins with a different serum PSA value, a steep branch would appear until it was readjusted. Additionally, it can be seen in FIGS. 4A-F that the evolution of the tumoral volume and that of serum PSA follow similar dynamics. This behavior is typically seen in low- and intermediate-risk tumors. Nonetheless, the connection between tumor growth and serum PSA dynamics is an ongoing major debate in the urologic community. Regular screening of PCa relies on PSA tests but, even though most prostatic adenocarcinomas grow showing a parallelism between the tumor volume and PSA levels in blood, it is known that there exists a certain degree of divergence between the dynamics of these two variables. This may even reach the limit of patients with low PSA and high tumoral masses in their prostates, or vice versa. Advanced and metastatic PCa may also exhibit almost no connection between serum PSA and tumor burden. However, PSA screening has greatly improved the early detection and treatment of PCa, leading to higher rates of incidence and an improved efficiency in its management worldwide. This biomarker has, therefore, been implemented in a mathematical model of PCa, as it permits direct connection with existing clinical data.

The model described herein may be expanded and improved in many different ways. First of all, several cancerous species could be considered, for instance, normoxic, hypoxic and necrotic, so as to better reproduce the shape instability. The model could also account for other substances that are known to have a role in PCa, such as oxygen or testosterone. Haptotaxis could play a role in more aggressive PCa and the invasiveness of PCa could be better reproduced if the diffusive term in equation [1] is defined in a more sophisticated fashion. PSA modeling in the medical community may be worth revisiting in order to find further connections between tumor shape and volume and PSA production, hence improving the definition of the rates $\alpha_h$ and $\alpha_c$, or suggesting a refinement of equation [4]. Modeling and simulation of the effects of radiation therapy in PCa may also be incorporated into the model, following previous studies carried out for low grade gliomas and glioblastoma multiforme.

Embodiments of the present disclosure may be realized in any of various forms. For example, some embodiments may be realized as a computer-implemented method, as a computer-readable memory medium, or as a computer system. Other embodiments may be realized using one or more custom-designed hardware devices such as ASICs. Still other embodiments may be realized using one or more programmable hardware elements such as FPGAs.

In some embodiments, a non-transitory computer-readable memory medium may be configured so that it stores program instructions and/or data, where the program instructions, when executed by a computer system, cause the computer system to perform a method, e.g., any of a method embodiments described herein, or, any combination of the method embodiments described herein, or, any subset of any of the method embodiments described herein, or, any combination of such subsets.

In some embodiments, a computer system may be configured to include a processor (or a set of processors) and a memory medium, where the memory medium stores program instructions, where the processor is configured to read and execute the program instructions from the memory medium, where the program instructions are executable to implement a method, e.g., any of the various method embodiments described herein (or, any combination of the method embodiments described herein, or, any subset of any of the method embodiments described herein, or, any combination of such subsets).

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method of modeling progression of prostate cancer in a subject, comprising:
   performing operations on a computer system to generate a tumor growth model for a prostate gland of the subject, wherein the operations include:
      simulating evolution of a tumor in the prostate gland of the subject, wherein said simulating of the evolution of the tumor is based at least on a coupled system of reaction-diffusion equations and a patient-specific geometric model of the prostate gland of the subject, wherein at least one of the reaction-diffusion equations is an equation representing the dynamics of tissue prostate-specific anitgen (PSA) $p(x,t)$, and wherein a value $p(x,t)$ of the tissue PSA field p represents a tissue PSA concentration at position x and time, and wherein the equation representing the dynamics of tissue PSA $p(x,t)$ includes one or more of the following:
         a term that represents a rate at which healthy cells produce PSA;
         a term that represents a rate at which cancerous cells produce PSA; and
         a decay term that represents a natural decay of the tissue PSA.

2. The method of claim 1, wherein the patient-specific geometric model is designed based on one or more medical images of the prostate gland of the subject.

3. The method of claim 1, wherein the patient-specific geometric model comprises a three-dimensional tensor-product spline.

4. The method of claim 1, wherein said simulating of the evolution of the tumor is performed according to a finite element method, or isogeometric analysis, or a finite difference method, or a finite volume method, or a mesh-free method, or an immersed method.

5. The method of claim 1, wherein the patient-specific geometric model is constructed based on a discretization method used for constructing geometric models and/or solving partial differential equation mathematical models on geometric models.

6. The method of claim 1, wherein one or more of the reaction-diffusion equations include: an equation representing dynamics of an evolution of a tumor phase field $\phi$ or an equation representing dynamics of a nutrient field $\sigma$, wherein a value $\phi(x,t)$ of the tumor phase field $\phi$ represents an extent to which cells at position x and time t are cancerous, and wherein a value $\sigma(x,t)$ of the nutrient field $\sigma$ represents a nutrient concentration at position x and time t.

7. The method of claim 6, wherein the operations further include one or more of the following:
   analyzing an output dataset representing the evolution of the tumor phase field $\phi$, the nutrient field $\sigma$, and the tissue PSA field p on the geometric model over an interval in simulated time to estimate a real-world time at which the tumor will:
      penetrate a capsule of the prostate gland of the subject;
      invade a tissue outside (or near) the prostate gland of the subject;
      reach a specified part of the prostate gland of the subject;
      transition from ellipsoidal growth to fingered growth; or
      make contact with the urethra of the subject; and
   outputting the real-world time or an indication of the real-world time via an output device.

8. The method of claim 6, wherein the operations further include one or more of the following:
   generating a video based on at least a portion of an output dataset representing the evolution of the tumor phase field $\phi$, the nutrient field $\sigma$, and the tissue PSA field p on the geometric model over an interval in simulated time, wherein the video illustrates evolution of a boundary of the tumor over time; and
   displaying the video via a display device.

9. The method of claim 6, wherein the operations further include one or more of the following:
   generating an image based on an output dataset representing the evolution of the tumor phase field $\phi$, the nutrient field $\sigma$, and the tissue PSA field p on the geometric model over an interval in simulated time, wherein said image illustrates a cross section through the geometric model, wherein image includes one or more curves corresponding a boundary of the tumor; and
   displaying the image via display device.

10. The method of claim 6, wherein the operations further include one or more of the following:
   generating a 3D rendering of the prostate gland and the tumor based at least on an output dataset representing the evolution of the tumor phase field $\phi$, the nutrient field $\sigma$, and the tissue PSA field p on the geometric model over an interval in simulated time and the geometric model; and
   displaying the 3D rendering via a display device.

11. The method of claim 6, wherein the operations further include one or more of the following:
   estimating a stage of prostate cancer development in the subject based on an output dataset representing the evolution of the tumor phase field $\phi$, the nutrient field $\sigma$, and the tissue PSA field p on the geometric model over an interval in simulated time and multiparametric magnetic resonance imaging (MRI) image data of the prostate gland of the subject; and
   displaying an indication of the estimated stage.

12. The method of claim 6, wherein the operations further include:
   computing a boundary of the tumor based on a level set of the phase field; and
   displaying the boundary of the tumor via a display device.

13. The method of claim 6, wherein the operations further include:
   computing a boundary of the tumor based on a level set of the phase field;
   computing a volume of the tumor based on the computed boundary; and
   displaying an indication of the computed volume.

14. The method of claim 6, wherein the operations further include projecting a three-dimensional field onto a model space corresponding to the geometric model, to approximate the initial tumor with the phase field.

15. The method of claim 6, wherein the operations further include:
   controlling a robotic surgical tool based on an output dataset representing the evolution of the tumor phase field $\phi$, the nutrient field $\sigma$, and the tissue PSA field p on the geometric model over an interval in simulated time in order to remove at least a portion of the tumor.

16. The method of claim 6, wherein the operations further include:
   determining an insertion path of a biopsy needle based on an output dataset representing the evolution of the tumor phase field $\phi$, the nutrient field $\sigma$, and the tissue PSA field p on the geometric model over an interval in simulated time, in order to increase a likelihood of obtaining samples of tumor tissue; and
   displaying an image or video indicating the insertion path.

17. The method of claim 1, wherein the equation representing the dynamics of tissue PSA p(x,t) includes one or more of the following:
   a term that is proportional to 1−$\phi$, wherein a value $\phi$(x,t) of a tumor phase field $\phi$ represents an extent to which cells at position x and time t are cancerous;
   a term that is proportional to the phase field $\phi$;
   a term that is proportional to a negative of the tissue PSA field.

18. A non-transitory memory medium storing program instructions, wherein the program instructions, when executed by a computer system, cause the computer system to perform the method comprising:
   generating a tumor growth model for a prostate gland of a subject, wherein generating the tumor growth model includes:
      simulating evolution of a tumor in the prostate gland of the subject, wherein said simulating of the evolution of the tumor is based at least on a coupled system of reaction-diffusion equations and a patient-specific geometric model of the prostate gland of the subject, wherein at least one of the reaction-diffusion equations is an equation representing the dynamics of tissue prostate-specific antigen (PSA) p(x,t), and wherein a value p(x,t) of the tissue PSA field p represents a tissue PSA concentration at position x and time t, and wherein the equation representing the dynamics of tissue PSA p(x,t) includes one or more of the following:
         a term that is proportional to 1−$\phi$, wherein a value $\phi$(x,t) of a tumor phase field $\phi$ represents an extent to which cells at position x and time t are cancerous;
         a term that is proportional to the phase field $\phi$; and
         a term that is proportional to a negative of the tissue PSA field.

19. A computer system comprising:
   a processor; and
   memory storing program instructions, wherein the program instructions, when executed by a processor, cause the processor to generate a tumor growth model for a prostate gland of the subject by:
      simulating evolution of a tumor in the prostate gland of the subject, wherein said simulating of the evolution of the tumor is based at least on a coupled system of reaction-diffusion equations and a patient-specific geometric model of the prostate gland of the subject, wherein at least one of the reaction-diffusion equations is an equation representing the dynamics of tissue prostate-specific antigen (PSA) p(x,t), and wherein a value p(x,t) of the tissue PSA field p represents a tissue PSA concentration at position x and time t, and wherein the equation representing the dynamics of tissue PSA p(x,t) includes one or more of the following:
         a term that is proportional to 1−$\phi$, wherein a value $\phi$(x,t) of a tumor phase field $\phi$ represents an extent to which cells at position x and time t are cancerous;
         a term that is proportional to the phase field $\phi$; and
         a term that is proportional to a negative of the tissue PSA field.

* * * * *

UNITED STATES PATENT AND TRADEMARK OFFICE
CERTIFICATE OF CORRECTION

PATENT NO. : 11,631,502 B2
APPLICATION NO. : 16/327875
DATED : April 18, 2023
INVENTOR(S) : Thomas J. R. Hughes, Hector Gomez and Guillermo Lorenzo Page 1 of 1

It is certified that error appears in the above-identified patent and that said Letters Patent is hereby corrected as shown below:

In the Claims

Claim 1, Column 20, Line 16, delete "anitgen" and substitute --antigen--.

Signed and Sealed this
Twenty-fifth Day of July, 2023

Katherine Kelly Vidal
*Director of the United States Patent and Trademark Office*